United States Patent
Guo et al.

(10) Patent No.: US 10,067,150 B2
(45) Date of Patent: Sep. 4, 2018

(54) METHOD AND PARTICLE ANALYZER FOR MEASURING A LOW CONCENTRATION PARTICLE SAMPLE

(75) Inventors: Wenheng Guo, Shenzhen (CN); Baohua Yan, Shenzhen (CN); Tao Shen, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 1132 days.

(21) Appl. No.: 13/339,251

(22) Filed: Dec. 28, 2011

(65) Prior Publication Data

US 2012/0171714 A1 Jul. 5, 2012

(30) Foreign Application Priority Data

Dec. 31, 2010 (CN) .......................... 2010 1 0619703

(51) Int. Cl.
*G01N 15/14* (2006.01)
*G01N 35/00* (2006.01)

(52) U.S. Cl.
CPC ....... *G01N 35/00623* (2013.01); *G01N 15/14* (2013.01); *G01N 2035/00366* (2013.01); *G01N 2035/00465* (2013.01)

(58) Field of Classification Search
CPC .................. G01N 33/49; G01N 21/49; G01N 2015/0065; Y10T 436/11

USPC ........................................................... 435/29
See application file for complete search history.

(56) References Cited

U.S. PATENT DOCUMENTS

| 5,939,326 | A | 8/1999 | Chupp et al. |
| 6,139,800 | A | 10/2000 | Chandler |
| 8,192,995 | B2 | 6/2012 | Zhang et al. |
| 2008/0041140 | A1* | 2/2008 | Uchihashi et al. .......... 73/61.71 |
| 2008/0187990 | A1 | 8/2008 | Nagai et al. |
| 2008/0241957 | A1 | 10/2008 | Shibata et al. |
| 2008/0293146 | A1 | 11/2008 | Frazier et al. |
| 2009/0035873 | A1* | 2/2009 | Shibata .................... G01N 1/38 436/179 |

FOREIGN PATENT DOCUMENTS

| CN | 101097180 A | 1/2008 |
| CN | 101387599 A | 3/2009 |
| CN | 101842688 A | 9/2010 |
| JP | 2009258071 A | 11/2009 |

OTHER PUBLICATIONS

Shet A. Characterizing blood microparticles: technical aspects and challenges. Vascular Health and Risk Management. 2008;4(4):769-774.*

* cited by examiner

*Primary Examiner* — Lynn Y Fan
(74) *Attorney, Agent, or Firm* — Kory D. Christensen; Polsinelli LLP

(57) ABSTRACT

A method and particle analyzer for measuring a low concentration particles sample disclosed.

12 Claims, 4 Drawing Sheets

METHOD AND PARTICLE ANALYZER FOR MEASURING A LOW CONCENTRATION PARTICLE SAMPLE

CROSS-REFERENCE TO RELATED APPLICATIONS

This application claims the benefit of Chinese Patent Application No. 201010619703.4, filed Dec. 31, 2010, which is incorporated herein by reference in its entirety.

TECHNICAL FIELD

The following disclosure relates to particle analyzers.

SUMMARY OF THE INVENTION

A particle analyzer and a method for measuring a low concentration particle sample are disclosed.

DETAILED DESCRIPTION

Figure 1:
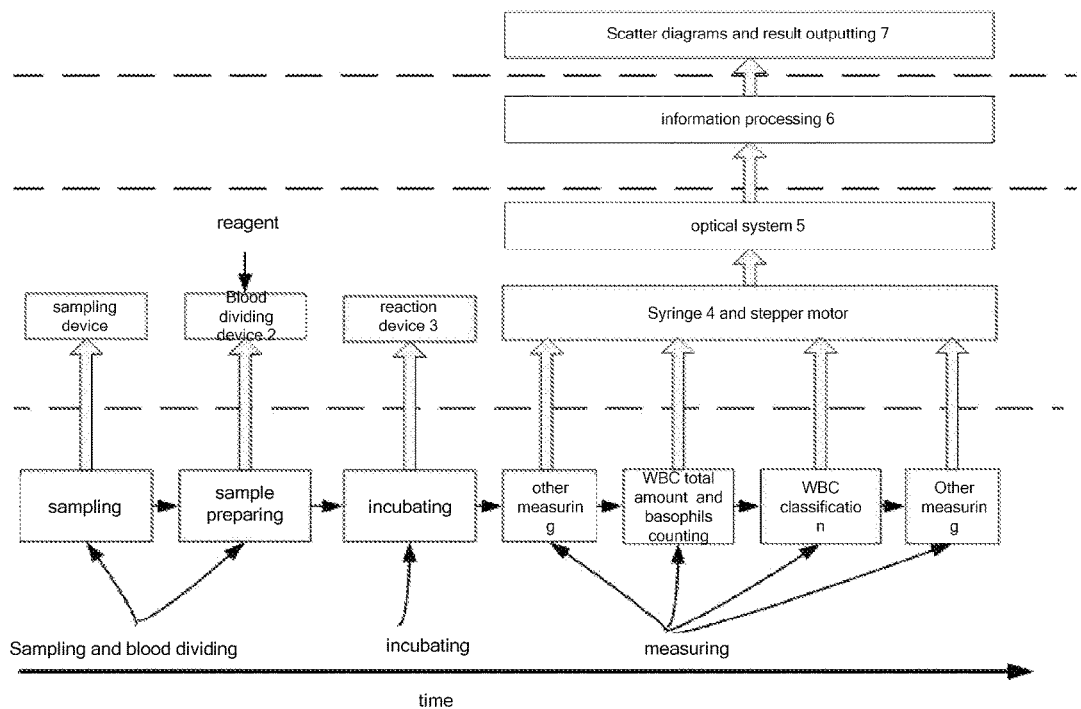
FIG. 1 is a flow diagram of a particle analyzer.

Particle analyzers are used for analyzing body fluids, such as blood or urine, to obtain scatter diagrams of different particles or a specific particle in the body fluid, as well as to obtain the total number of particles. A particle analyzer used for measuring blood cells or other body fluid cells is usually referred to as a cell analyzer. FIG. 1 is a flow diagram of a basic measurement procedure used by a cell analyzer for analyzing blood cells.

Initially, during a sampling and blood dividing stage, a sampling device collects blood samples or other samples to be analyzed, after which a blood division device 2 divides the samples into a number of sub-samples for different testing purposes. For example, the blood division device may divide 20 μL of sample for determining a total white blood cell count and Basophils count, while dividing another 20 μL of sample for classifying other white blood cells.

An incubation stage follows the sampling and blood dividing stage in which the sub-samples and their respective reagents are injected to a reaction device 3 for incubation.

A measuring stage follows the incubation stage, which includes total white blood cell counting and Basophils counting, as well as a white blood cell classifying stage. For example, after a certain period of reaction, 20 μL of sample and 1 mL of reagent mixture are injected into an optical system 5 for the total white blood cell count and Basophils count. Thereafter, 50 μL of mixture is injected by a syringe. The sub-sample passes through the optical system 5 and information processing unit 6, and a scatter diagram 7 of the total white blood cell count is output.

A concentration of the white blood cells of the final sample is obtained according to a total volume injected by syringe 4, a volume measured, and a dilution factor. Thereafter, another incubated 20 μL of sub-sample and 1 mL of reagent mixture is injected into the optical system 5 through a syringe 4 for leucocytes classification. The sub-sample passes the optical system 5 and the information processing unit 6, and a scatter diagram 7 of white blood cell classification is output. For the scatter diagram 7 of white blood cell classification, the more points there are in the diagram (representing counted cells), the better the classification result. Normal white blood cell samples have a concentration over 4000/μL, and a concentration of over 3000 is better for white blood cell classification.

The blood cells may come from whole blood, peripheral blood, or body fluid. If the sample is from peripheral blood, no more than 40 μL blood will be usually collected in hospitals. The cell analyzer generally uses more than 100 μL of blood. Accordingly, the blood sample usually needs to be diluted over four times before measurement. For a body fluid sample, the collected sample volume may meet the analysis requirement, but the concentration of the sample itself is low. For example, in a normal blood sample test, 50 μL of sample is injected and 40 μL of sample is counted. If a dilution ratio is 50, then 40 μL/50=0.8 μL of sample is actually counted. For the blood sample with 6000/μL concentration of white blood cells, 4800 white blood cells are counted. However, if the sample is from peripheral blood, only 1200 white blood cells are counted, and the result will have decreased accuracy.

This following disclosure provides a method and device for measuring a low concentration particle sample and a particle analyzer that overcomes the above-mentioned deficiencies.

According to one embodiment, a method for measuring a low concentration particle sample includes: mixing and incubating the low concentration particle sample and a corresponding reagent; passing the incubated sample through a measuring system in a set low concentration measuring time, the low concentration measuring time being Δt greater than a normal sample measuring time; and outputting a particle analysis result obtained from the measuring system.

According to one embodiment, a particle analyzer is disclosed, which includes a sample preparing system configured to mix a low concentration sample and a corresponding reagent according to a set dilution ratio and configured to incubate the mixed sample for a set duration; a measuring system configured to measure the incubated sample in a set low concentration sample measuring time, in which the low concentration sample measuring time is ΔT longer than normal measuring time; and an information processing system configured to process the signal output from the measuring system and output a particle analysis result.

In one embodiment, the measuring system includes an optical system having a measuring chamber, which is configured to measure samples passing the measuring chamber under light beams, and a current limiter configured to transport the incubated sample to the optical system in the set low concentration sample measuring time.

In one embodiment, the current limiter includes a syringe and a motor to drive the syringe. The motor drives the syringe to inject the incubated sample to the optical system during a period that is in accordance with the low concentration sample measuring time.

In one embodiment, the particle analyzer further includes a sample measuring time confirming device, which is configured to receive a user selection as to whether the sample to be measured is a normal sample or a low concentration sample, and, according to predetermined sample-to-measuring-time relationship, obtain the measuring time of the sample.

In another embodiment, the particle analyzer further includes a sample distributing system, which is configured to divide the sample into at least two parts according to a pre-determined volume. The sample preparing system controls the latter sample according to the time cost of incubation from short to long to begin at least $\Delta T$ delayed than the former sample, $\Delta T$ being a delay time for measuring time for the former sample compared to a normal sample.

The disclosed method and device improves the accuracy of sample measurement by increasing the measuring time and increasing the number of measured particles.

As used herein, a "low concentration sample" indicates a sample with a concentration of particles to be measured that is lower than a normal sample. For example, for a blood cell sample, white blood cells are the particles to be measured. In a normal full blood sample, the concentration of white blood cells is about 4000-10000/μL. If the concentration white blood cells is lower than 4000/μL, then the sample may be regarded as a low concentration sample. The specific number can change according to different situations. Increasing measuring time will increase the sample volume passing through the measuring system, so as to increase the number of particles to be measured.

A particle analyzer used to analyze cells is illustrated as an example, but other types of particle analyzers operate using similar principles.

Figure 2:
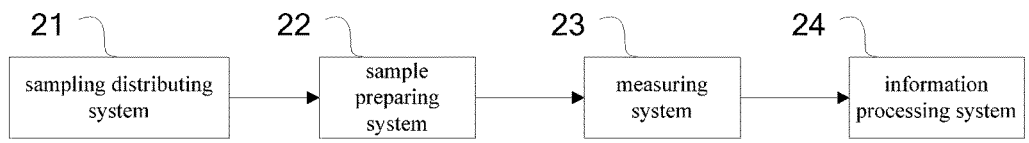
FIG. 2 is a block diagram of a particle analyzer.

One embodiment of a particle analyzer is shown in FIG. 2. The particle analyzer includes a sample preparing system 22, a measuring system 23, and an information processing system 24. In other embodiments, the particle analyzer may further include a sample distributing system 21. The sample distributing system 21 is configured to divide the sample into at least two parts according to a pre-determined volume.

The sample preparing system 22 is configured to mix a low concentration sample and a corresponding reagent according to a set dilution ratio and to incubate the mixed sample for a set duration. In one embodiment, the sample preparing system 22 includes a reaction cell, and the mixed sample is incubated in the reaction cell.

In one embodiment, the measuring system 23 is configured to measure the incubated sample according to a set low concentration sample measuring time. The measuring system 23 may include an optical system having a measuring chamber and a current limiter. The optical system may include a measuring chamber and an optical signal transceiver. The optical transceiver is used for sending and/or receiving optical signals. The measuring chamber is within the region of illumination. During the measurement process, the sample flow is embraced by a sheath flow and passes the measuring chamber, and the particles in the sample flow generate different optical signals when illuminated. The transceiver receives the optical signals and converts them into corresponding electrical signals.

The current limiter is used for transporting a certain volume of the incubated sample into the measuring chamber. In one embodiment, the current limiter includes a syringe and a motor to drive the syringe. The motor drives the syringe to continuously inject the incubated sample into the optical system for a period in accordance with the low concentration sample measuring time. The sample in the sheath flow passes the measuring chamber. The sample is driven by the syringe, and the syringe is driven by the motor. By controlling a rotating speed (step/second) of the motor and the measuring time, a total volume of the measured sample can be obtained. In one embodiment, the motor is a step motor. Because the rotating speed is related the total steps, for the same syringe, each step equals a fixed liquid volume. Therefore, a total volume of the measured sample can be obtained. In the illustrated embodiment, the rotating speed of the motor or the injecting volume of sample per unit time are not increased, and a width of the measured sample flow is not changed so as to not reduce the accuracy of the measurement result.

In other embodiments, the current limiter may further include a pressure source or vacuum chamber. The pressure source generates a pressure to push the incubated sample into the optical system. The vacuum chamber can generate a relatively negative pressure to inhale the incubated sample into the optical system. By these methods, the incubated sample is embraced by the sheath flow and passes the measuring chamber.

The information processing system 24 is used for processing the signal output from the measuring system and for outputting a particle analysis result according to the total amount of the sample and the dilution ratio.

As noted above, when blood cells are tested by a particle analyzer, the cells may originate from a full blood sample, a peripheral blood sample, and/or a body fluid sample. If the cells originate from a peripheral blood sample, the sample volume will be usually no more than 40 μL in most hospitals. However, the blood analyzer generally needs more than 100 μL of blood sample. Accordingly, the sample is often diluted over four times before measurement. For the body fluid sample, the volume collected may meet the analyzing requirement, but the concentration of the sample itself is low. Therefore, samples from peripheral blood or body fluid are low concentration samples.

When the sample to be measured is a low concentration sample, the measuring system measures the incubated sample in a set low concentration sample measuring time. To increase the amount of particles to be measured, the low concentration sample measuring time is $\Delta T$ longer than a normal measuring time.

Figure 3:
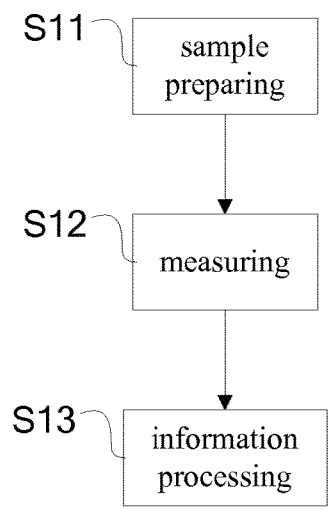
FIG. 3 is a flow diagram of a particle analyzer.

FIG. 3 is a flow diagram of a method for low concentration measuring.

Step S11, sample preparing. The low concentration sample and the corresponding reagent are mixed according to a set ratio and incubated for a set time.

Step S12, measuring. The incubated sample passes the measuring system in the low concentration sample measuring time. The low concentration sample measuring time is $\Delta T$ longer than normal sample measuring time, $\Delta T$ being greater than zero. The period of $\Delta T$ is based on experience, which can be determined according to a concentration differential between the low concentration sample and the normal sample, and a minimum number of particles to be measured. For instance, for white blood cells, the minimum number of particles should be greater than 3000. When a concentration of the particles to be measured in the normal sample is over four times that in the low concentration sample, the low concentration sample measuring time is 2.5 times the normal sample. Longer measuring times are better, but considering the measuring efficiency, the low concentration sample measuring time can be, for example, 2 to 6 times the normal sample.

Step S13, information processing. The measuring signals output by the measuring system are processed, and the particle analysis result is output. The result may be a scatter diagram of the total white blood cells and/or differential white blood cells.

In one embodiment, because the current limiter inputs a certain volume of sample in one unit time, and the working time is certain, the total volume of the sample into the optical system in a certain working time can be determined. The greater the working time is, the greater the volume of sample that enters into the measuring chamber, and the more particles the optical system measures. Therefore, the measurement accuracy can be improved through increasing the amount of particles to be measured.

Figure 4:
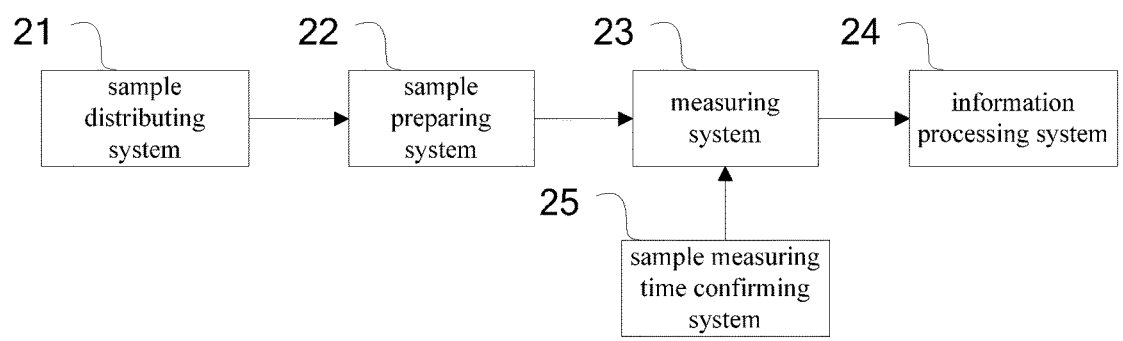
FIG. 4 is a block diagram of a particle analyzer.

In another embodiment, as shown in FIG. 4, the particle analyzer further includes a sample measuring time confirming device 25, which is configured to receive user input as to whether the sample to be measured is a normal sample or a low concentration sample, and, according to a predetermined sample type-measuring time relationship, to determine the measuring time of the sample. The current limiter takes the determined measuring time as the working time. During the working time, the incubated sample is continuously moved into the optical system. For example, the stepper motor drives the syringe to inject the incubated sample into optical measuring device according to the determined measuring time.

The sample to be measured may be a normal sample or a low concentration sample. Users may be permitted to choose the sample type by an input device, such as a keyboard or graphical user interface (GUI), after which the particle analyzer may select the measurement mode according to sample type. When a user chooses a normal sample type, the confirming device receives the selection and determines the measuring time as normal sample measuring time. The particle analyzer then operates according to the normal procedure, as shown in FIG. 5.

Figure 6:
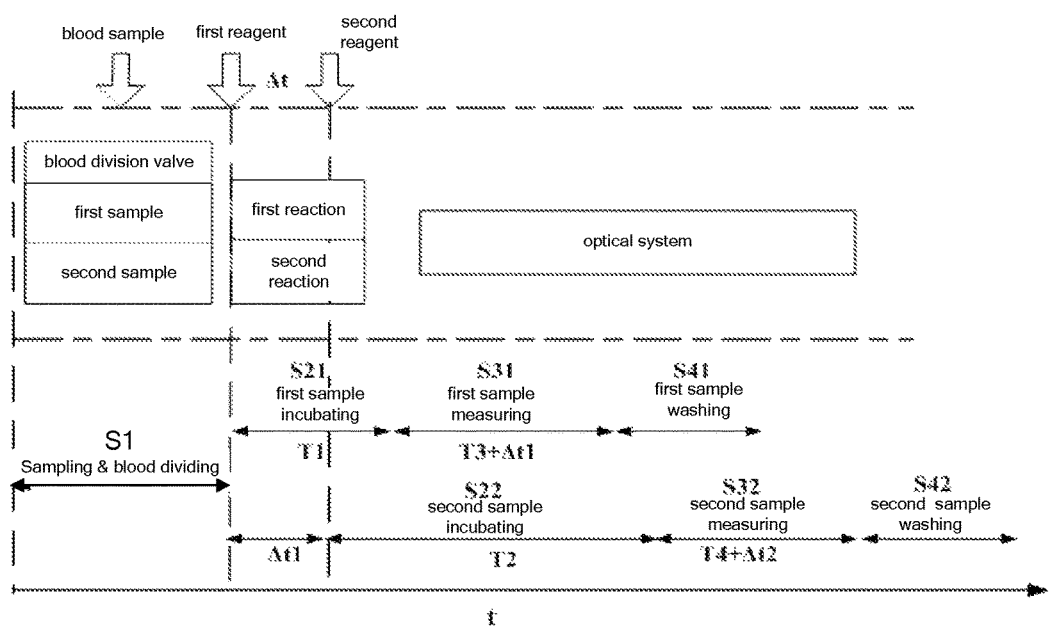
FIG. 6 is a flow diagram for measuring a low concentration blood sample.

In order to improve the low concentration sample measuring performance, when the sample is a pre-diluting sample, body fluid, or other low concentration sample, the user can choose a low concentration measurement mode. The particle analyzer works according to the low concentration sample measuring procedure, as shown in FIG. 6.

The following description explains the differences between the normal procedure and low concentration sample procedure, using blood sample analysis as an example.

Figure 5:
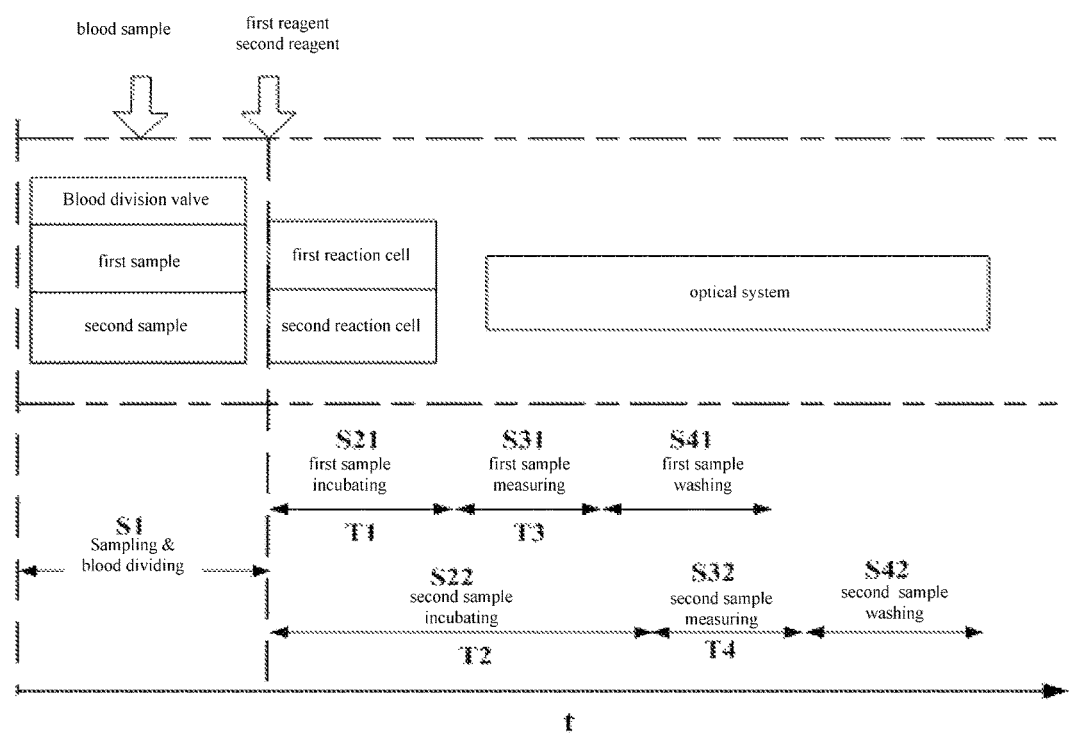
FIG. 5 is a flow diagram for measuring a normal blood sample.

According to the normal sample procedure shown in FIG. 5, in time sequence, S1 is the sampling and dividing stage, including a sampling sub-stage and a blood division sub-stage. The sample distributing system includes a sampling device and blood division device. In the sampling sub-stage, the sampling device collects the sample into the blood analyzer device, e.g., 150 μL of sample is collected, and stores the blood sample in the blood division device. Generally, the blood division device is a blood division valve. The blood division sub-stage follows the sampling sub-stage, with the blood sample being divided into plural parts through the blood division valve. For example, the blood sample is divided into a first sample and a second sample, and the first sample is for a total white blood cell count with a volume of 20 μL, and the second sample is for white blood cell classification with a volume of 20 μL.

The incubating stage follows the blood dividing sub-stage. The divided sample and the corresponding reagent are moved into the reaction cell for incubation. For example, the first sample is moved into a first reaction cell by a first reagent, and the second sample is moved into a second reaction cell by a second reagent. In this process, other reagents may be injected into the first or second reaction cell individually.

S21 represents the incubating process of the first sample and the first reagent, and S22 represents the incubating process of the second sample and the second reagent. T1 represents an incubating time for the first sample. T2 represents an incubating time for the second sample. In one embodiment, the time period of T1 or T2 is fixed; otherwise, the consistency of the analyzer system is disturbed.

When the incubation time of the first sample and first reagent arrives at the end of T1, the first sample enters into measuring stage S31. When the incubation time of the second sample and second reagent arrives at the end of T2, the second sample enters to measuring stage S32. Because the first sample and the second sample are measured in a common optical system, the measuring stages S31 and S32 are completed in sequence. Here, assuming S31 is ahead of S32, T3 is the measuring time for the first sample, and T4 is measuring time for the second sample.

When S31 and S32 are finished, the first sample and second sample enter to the washing stages S41 and S42, respectively.

If the sample originates from peripheral blood, no more than 40 μL will be usually collected in hospitals. Therefore, it generally needs to be pre-diluted, such as, for example, diluted four times to 160 μL to meet a requirement for 150 μL of suction volume, which causes the sample to become a low concentration sample.

For the low concentration sample, the measuring time is greater than that of the normal sample. For example, the measuring time of the first sample may be increased from T3 to T3+Δt1, and the measuring time of the second sample may be increased from T4 to T4+Δt2. Assuming, in this example, that T3=5 seconds, Δt1=10 seconds, T4=5 seconds, and Δt2=10 seconds, then for the first sample and the second sample, the measuring time is increased from five seconds to 15 seconds, which is three times the normal measuring time. As for the above mentioned blood sample with a concentration of white blood cells of 6000/μL, 3600 particles can be measured and an improved measuring performance can be obtained.

According to the low concentration sample procedure shown in FIG. 6, in the sampling and blood dividing stage S1, the blood sample is collected and divided into, for example, two parts including a first sample and the second sample. Thereafter, the first sample and the second sample enter the incubating stages S21 and S22, respectively, in which both are mixed with corresponding reagents in different reaction cells.

In one embodiment, because the first sample and the second sample are measured in a common optical system, the second sample measuring must wait for the first sample measuring to be completed. In this case, if the adding time of the reagent for the second sample does not change, the corresponding incubating time will be increased to be greater than T2. Therefore, the accuracy of the measuring for the second sample may decline.

To avoid this problem, the incubating time for the second sample is kept unchanged and the measuring time for the first sample is increased. The adding time of the reagent for the second sample is Δt time delayed from that in the normal sample measuring mode, in which Δt is not less than Δt1. In other words, the second sample is Δt time delayed in the starting time of incubation. Therefore, the second sample has a coherent incubating time in the normal sample mode as well as in the low concentration sample mode. For the second sample, the measuring time also needs to be increased. If there is a third sample to be measured, in order to keep the incubating time of the third sample unchanged, the beginning time of the incubation for the third sample is also delayed by a period of Δt to the beginning time of the incubation for the second sample.

In one embodiment, the first sample completes incubation and goes into the measuring stage S31. The first sample has a measuring time of T3+Δt1, which is Δt1 more than normal sample measuring time. In one embodiment, for example, by controlling the current limiter working time to control the measuring time of the first sample, the measuring time of the first sample is controlled by controlling the working time of the motor that drives the syringe. The second sample has an incubating time delayed at least Δt1, so the first sample has completed measurement when the second sample completes incubation and goes into the measuring stage S32. The measuring time for the second sample is T4+Δt2, which is Δt2 more than normal sample measuring time.

When the stages S31 and S32 are finished, the first sample and the second sample enter into washing stages S41 and S42, respectively.

The present disclosure can increase the amount of particles to be measured by increasing the measuring time and, without changing the dilution ratio, improving the measuring performance. It is cost effective in that no extra components/modules are required in some embodiments.

This disclosure has been made with reference to various exemplary embodiments including the best mode. However, those skilled in the art will recognize that changes and modifications may be made to the exemplary embodiments without departing from the scope of the present disclosure. For example, various operational steps, as well as components for carrying out operational steps, may be implemented in alternative ways depending upon the particular application or in consideration of any number of cost functions associated with the operation of the system, e.g., one or more of the steps may be deleted, modified, or combined with other steps.

Additionally, as will be appreciated by one of ordinary skill in the art, principles of the present disclosure may be reflected in a computer program product on a computer-readable storage medium having computer-readable program code means embodied in the storage medium. Any tangible, non-transitory computer-readable storage medium may be utilized, including magnetic storage devices (hard disks, floppy disks, etc.), optical storage devices (CD-ROMs, DVDs, Blu-ray Discs, etc.), flash memory, etc. The computer program instructions may be loaded onto a general purpose computer, special purpose computer, or other programmable data processing apparatus to produce a machine, such that the instructions that execute on the computer or other programmable data processing apparatus create means for implementing the functions specified. These computer program instructions may also be stored in a computer-readable memory that can direct a computer or other programmable data processing apparatus to function in a particular manner, such that the instructions stored in the computer-readable memory produce an article of manufacture, including implementing means that implement the function specified. The computer program instructions may also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

While the principles of this disclosure have been shown in various embodiments, many modifications of structure, arrangements, proportions, elements, materials, and components that are particularly adapted for a specific environment and operating requirements may be used without departing from the principles and scope of this disclosure. These and other changes or modifications are intended to be included within the scope of the present disclosure.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof are intended to cover a non-exclusive inclusion, such that a process, a method, a system, an article, or an apparatus that comprises a list of elements does not include only those elements but may include other elements not expressly listed or inherent to such process, method, system, article, or apparatus. Also, as used herein, the terms "coupled," "coupling," and any other variation thereof are intended to cover a physical connection, an electrical connection, a magnetic connection, an optical connection, a communicative connection, a functional connection, and/or any other connection.

Those having skill in the art will appreciate that many changes may be made to the details of the above-described embodiments without departing from the underlying principles of the invention. The scope of the present invention should, therefore, be determined only by the following claims.

What is claimed is:

1. A method for measuring a low concentration particle sample, comprising:
    selecting a measuring mode of a measuring system corresponding to a low concentration sample type;
    dividing the low concentration particle sample into at least two parts according to a set volume by a sample distributing system;
    mixing and incubating a first part of the sample and a corresponding reagent;
    mixing and incubating a second part of the sample and a corresponding reagent;
    passing the incubated first and second parts of the sample through the measuring system set in the selected low concentration measuring mode; and
    outputting a particle analysis result obtained from the measuring system,
    wherein the two parts of the sample pass through the measuring system sequentially according to a length of incubation time for each part of the sample, and wherein the shorter an incubation time of the part of the sample is, the earlier the part of the sample will pass through the measuring system;
    wherein a measuring time of the low concentration measuring mode is predetermined by the measuring system and is longer than a measuring time of a higher concentration measuring mode by $\Delta t$, the $\Delta t$ being greater than zero; and
    wherein the step of mixing and incubating the second part of the sample starts later than the step of mixing and incubating the first part of the sample by at least the $\Delta t$, but before finishing measurement of the first part of the sample; and wherein an incubation time of the second part of the sample is longer than an incubation time of the first part of the sample.

2. The method according to claim 1, wherein passing the incubated sample through the measuring system comprises driving a syringe according to the low concentration particle sample measuring time to inject the incubated sample into an optical system.

3. The method according to claim 1, wherein the measuring time of the low concentration measuring mode is 2 to 6 times longer than the measuring time of the higher concentration measuring mode.

4. The method according to claim 1, wherein the low concentration particle sample is selected from a diluted whole blood sample or a body fluid sample.

5. The method according to claim 1, further comprising: mixing and incubating a third part of the sample and a corresponding reagent, wherein an incubation time of the third part of the sample is longer than an incubation time of the second part of the sample.

6. The method according to claim 1, wherein the low concentration particle sample comprises a white blood cell concentration of lower than 4000/µL.

7. A method of analyzing a blood or body fluid sample, comprising:
   obtaining a sample selected from a low concentration sample type and a sample type having a concentration higher than the low concentration sample type;
   selecting a measuring mode corresponding to the sample type;
   dividing the obtained sample selected from a low concentration sample type and a sample type having a concentration higher than the low concentration sample type into at least two parts;
   mixing and incubating a first part of the obtained sample and a corresponding reagent;
   mixing and incubating a second part of the obtained sample and a corresponding reagent;
   passing the incubated first and second parts of the obtained sample through a measuring system having a measuring time that is predetermined according to the selected measuring mode; and
   outputting a particle analysis result obtained from the measuring system,
   wherein the two parts of the sample pass through the measuring system sequentially according to a length of incubation time for each part of the sample, and wherein the shorter an incubation time of the part of the sample is, the earlier the part of the sample will pass through the measuring system;
   wherein a measuring time of the low concentration sample type is longer than a measuring time of the sample type having a concentration higher than the low concentration sample type by Δt, the Δt being greater than zero; and
   wherein the step of mixing and incubating the second part of the sample starts later than the step of mixing and incubating the first part of the sample by at least the Δt, but before finishing measurement of the first part of the sample when the measuring mode is selected for the low concentration sample type; and
   wherein the step of mixing and incubating the second part of the sample starts simultaneously with the step of mixing and incubating the first part of the sample when the measuring mode is selected for the sample type having a concentration higher than the low concentration sample type; and
   wherein an incubation time of the second part of the obtained sample is longer than an incubation time of the first part of the obtained sample in either of the selected measurement modes.

8. The method according to claim 7, wherein the low concentration sample type is selected from a diluted whole blood sample or a body fluid sample.

9. The method according to claim 7, wherein the low concentration sample type comprises a white blood cell concentration of lower than 4000/µL.

10. The method according to claim 7, further comprising:
    mixing and incubating a third part of the obtained sample selected from a low concentration sample type and a sample type having a concentration higher than the low concentration sample type and a corresponding reagent, wherein an incubation time of the third part of the obtained sample is longer than an incubation time of the second part of the obtained sample in either of the selected measurement modes.

11. The method according to claim 1, wherein the step of mixing and incubating the second part of the sample starts later than the step of mixing and incubating the first part of the sample by the Δt.

12. The method according to claim 7, wherein the step of mixing and incubating the second part of the sample starts later than the step of mixing and incubating the first part of the sample by the Δt, when the measuring mode is selected for the low concentration sample type.

* * * * *